United States Patent
Maquart et al.

(10) Patent No.: US 9,675,628 B2
(45) Date of Patent: Jun. 13, 2017

(54) METHOD FOR PRODUCING A MIXTURE OF NEUTRAL OLIGOSACCHARIDES EXTRACTED FROM FLAXSEED

(71) Applicants: UNIVERSITE DE REIMS CHAMPAGNE ARDENNE, Reims (FR); CENTRE VALORISATION GLUCIDES PROD NAT, Dury (FR); UNIVERSITE DE ROUEN, Mont-Saint-Aignan (FR); VANDEPUTTE OLEOCHEMICALS, Mouscron (BE); CENTRE NATIONAL DE LA RECHERCHE SCIENTIFIQUE, Paris (FR)

(72) Inventors: Francois Maquart, Reims (FR); Georges Bellon, Reims (FR); Claire Marchal, Rossfeld (FR); Helene Ducatel, Beauvoir (FR); Olivier Dupuis, Frevent (FR); Luc Picton, Grand Courronne (FR); Didier Lecerf, Bosc Roger sur Cuchy (FR); Renauld Forbice, Draguignan (FR)

(73) Assignees: UNIVERSITE DE REIMS CHAMPAGNE ARDENNE, Reims (FR); CENTRE VALORISATION GLUCIDES PROD NAT, Dury (FR); UNIVERSITE DE ROUEN, Mont-Saint-Aignan (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 14/786,833

(22) PCT Filed: Apr. 24, 2014

(86) PCT No.: PCT/FR2014/050994
§ 371 (c)(1),
(2) Date: Oct. 23, 2015

(87) PCT Pub. No.: WO2014/174220
PCT Pub. Date: Oct. 30, 2014

(65) Prior Publication Data
US 2016/0101120 A1   Apr. 14, 2016

(30) Foreign Application Priority Data
Apr. 24, 2013 (FR) ...................... 13 53718

(51) Int. Cl.
| | |
|---|---|
| A61K 31/702 | (2006.01) |
| A61K 36/55 | (2006.01) |
| A61K 8/60 | (2006.01) |
| A61K 8/97 | (2017.01) |
| A61Q 19/08 | (2006.01) |
| C12P 19/04 | (2006.01) |
| A61K 38/55 | (2006.01) |
| A61K 8/73 | (2006.01) |

(52) U.S. Cl.
CPC .............. *A61K 31/702* (2013.01); *A61K 8/60* (2013.01); *A61K 8/73* (2013.01); *A61K 8/97* (2013.01); *A61K 38/55* (2013.01); *A61Q 19/08* (2013.01); *C12P 19/04* (2013.01); *A61K 2236/39* (2013.01); *A61K 2800/594* (2013.01)

(58) Field of Classification Search
None
See application file for complete search history.

(56) References Cited

U.S. PATENT DOCUMENTS

| | | |
|---|---|---|
| 2004/0097464 A1 | 5/2004 | Robert et al. |
| 2007/0293433 A1 | 12/2007 | Lubrano et al. |

FOREIGN PATENT DOCUMENTS

| | | |
|---|---|---|
| WO | 93 16707 A1 | 2/1993 |
| WO | 99 24009 A1 | 5/1999 |
| WO | 2008 043944 A2 | 4/2008 |

OTHER PUBLICATIONS

Karine Guilloux et al: "Production of Arabinoxylan-oligosaccharides form Flaxseed (*Linum usitatissimum*)", Journal of Agricultural and Food Chemistry, vol. 57, No. 23, Dec. 9, 2009.
W. Wojtasik et al: "The significance of flax fibre pectin in the extracellular matrix remodelling of wound healing process", FEBS Journal, Blackwell Publishing, London, GB, vol. 279, No. Suppl 1, Sep. 1, 2012, p. 72.

*Primary Examiner* — Layla Berry
(74) *Attorney, Agent, or Firm* — Andrew W. Chu; Craft Chu PLLC

(57) ABSTRACT

The method for producing a mixture of neutral oligosaccharides extracted from flaxseed includes oligosaccharides having high molar masses generated by fractionation by ultrafiltration at a cut-off of between 15,000 and 50,000 Da and between 5,000 and 15,000 Da. The mixture of oligosaccharides produced as a result of the implementation of the method, and to the applications of the mixture can be used for skin repair and skin aging control.

19 Claims, 12 Drawing Sheets

| Samples | Code | MS(%) | Ash/MS | Prot/MS | Sulfates/MS | tot sugars/MS | Free sugars/MS | Uronics/MS | Barium/MS |
|---|---|---|---|---|---|---|---|---|---|
| After hydrolysis, neutralized, centrifuged | E1 | 0,91% | 0,00% | 11,42% | 0,21% | 73,60% | 14,90% | 11,21% | 0,22% |
| Centrifuged retentate 50 KD. (supernatant) | E3 | 2,73% | 5,30% | 3,60% | 0,01% | 42,70% | 0,70% | 28,24% | 0,72% |
| Concentrated permeate 50 KD | E2 | 1,49% | 0,90% | 12,55% | 0,36% | 85,30% | 19,80% | 4,17% | 0,02% |
| Centrifuged permeate 15 KD | E4 | 0,79% | 6,00% | 26,31% | 0,12% | 52,60% | 5,70% | 11,01% | 0,11% |
| Concentrated permeate 15 KD | E5 | 0,89% | 0,00% | 8,82% | 0,38% | 82,10% | 27,80% | 1,62% | |
| Centrifuged permeate 5 KD. | E6 | 1,10% | 0,50% | 9,78% | 0,29% | 86,30% | 19,70% | 1,34% | |
| Concentrated permeate 5 KD | E7 | 1,23% | 3,10 | 4,66% | 0,38% | 97,20% | 36,30% | 0,71% | |

FIG 1

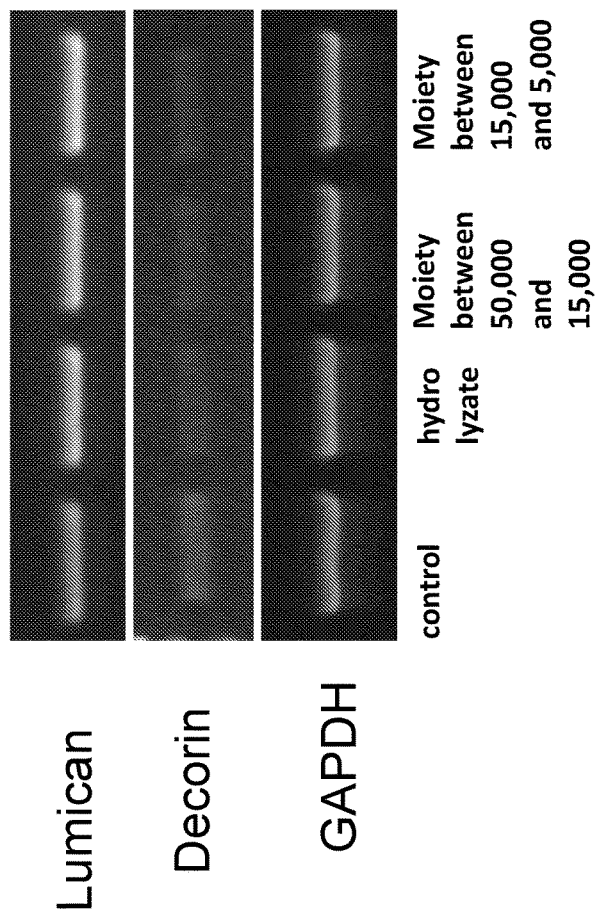

METHOD FOR PRODUCING A MIXTURE OF NEUTRAL OLIGOSACCHARIDES EXTRACTED FROM FLAXSEED

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The invention relates to the oligosaccharides, namely extracted from plants, and more particularly to the use of these oligosaccharides in the cosmetic or dermatological field.

The invention relates more particularly to a cosmetic or dermatological use of the neutral oligosaccharides extracted from flaxseed and a method for producing oligosaccharides for example after hydrolysis and fractionation of a solution of mucilage.

In particular, the neutral oligosaccharides extracted from flaxseed can namely be used to promote skin tissue repair and also to prevent the effects of skin aging.

Skin repair consists of a set of processes implemented with a view to repair damage or injury suffered by the skin and to reconstruct a tissue close to the original tissue being damaged.

Skin aging, in turn, is responsible for the modification of the anatomical and histological structures and the alteration of the cell functioning.

Skin aging results from several factors, namely a cell alteration, for example due to oxidative stress, but also from external factors such as pollution, tobacco or alcohol consumption, excessive exposure to sunlight, etc.

Skin aging results into the appearance of wrinkles and dark spots—generally brown—and a decrease in skin tonus.

2. Description of Related Art Including Information Disclosed Under 37 CFR 1.97 and 37 CFR 1.98.

The prior art provides a number of strategies for fighting the visible signs of skin aging. In this respect, the following techniques can namely be mentioned:

laser treatment for correcting the defects such as brown spots and fine wrinkles;

injections of botulinum toxin, hyaluronic acid or collagen;

peeling, which consists in removing a significant layer of the epidermis;

face-lift;

etc.

However, the currently existing techniques have a number of undesirable side effects and do not always permit to obtain satisfactory results.

Therefore, in recent years other strategies have been implemented by the laboratories in order to fight more effectively and more naturally the effects of skin aging and to try to slow down this process. It would also be necessary to find solutions for promoting skin tissue repair in case of injury.

In particular, the research on the use of oligosaccharides in the cosmetic compositions in order to reduce the signs of skin aging has been developed in recent years. Indeed, the sugar-based molecules are of particular interest, namely because of their moisturizing properties.

Thus, some patent applications relate to cosmetic compositions including oligosaccharides; in particular, patent application WO 99/24009 discloses namely the use of oligosaccharides containing xylose for increasing the synthesis of some compounds, the proteoglycans and the glycosaminoglycans. However, in this document, the xylose being used is a commercial product and not a natural product from the plant.

Patent document U.S. 2007/0293433 relates to an anti-aging composition including a plurality of oligosaccharides obtained by enzymatic hydrolysis of pectin, which is also a commercial product.

Also known, from patent application U.S. 2004/0097464, is a composition comprising a mixture of oligosaccharides, namely fucose, the latter being obtained by hydrolysis performed by a microorganism. The mixture of oligosaccharides described herein requires the implementation of a complicated method including a large number of steps, some of which require the action of pathogenic microorganisms, which must necessarily be removed from the mixture for cosmetic application.

In addition, the compositions described in the aforementioned documents do not have a sufficiently effective action, namely in the stimulation of skin repair for which few solutions exist in the prior art.

It is also known to use active substances extracted from plants, namely from flax (*Linum usitatissimum*), which plant belongs to the Linaceae family, for use in fighting aging signs.

Known from the international patent application WO 2008/043944 is thus the use of active substances extracted from flax for the preparation of a cosmetic composition for fighting skin aging, as well as a process for producing them.

However, the active substance obtained by the method described in this patent application includes a number of components, and in majority proteins having a molecular weight of less than 5,000 Da in high concentrations, monomeric sugars, uronic acids, carbohydrates, etc.

Therefore, this variety of components does not permit a targeted and specific action, and namely such a disparity of components does not permit to effectively promote the skin repair in case of damage to the skin.

BRIEF SUMMARY OF THE INVENTION

Within the framework of the present invention, the applicants have discovered that determined particular oligosaccharides extracted from flaxseed permit an effective stimulation of the phenomena implemented namely in the processes of skin tissue repair, and have developed a method for extracting these oligosaccharides.

More particularly, these are neutral oligosaccharides having a high molecular weight, the latter being obtained through fractionation by ultrafiltration at a cut-off point, on the one hand, between 5,000 and 15,000 Da and, on the other hand, between 15,000 and 50,000 Da.

Thus, the present invention relates to a method for obtaining a mixture of neutral oligosaccharides extracted from flaxseed, said oligosaccharides having high molecular weights, said method including the following steps:

- an hydrolysis at acidic pH is carried out on a solution of flax mucilage, the latter being obtained by extraction from flaxseed in a solvent;
- said solution is neutralized by adding a base in an adequate quantity;
- a first ultrafiltration of the solution through a membrane with a porosity of 50,000 Da is carried out, so as to obtain a first retentate and a first permeate;
- a second ultrafiltration of said first permeate through a membrane with a porosity of 15,000 Da is carried out, so as to obtain a second retentate and a second permeate;
- a third ultrafiltration of said second permeate through a membrane with a porosity of 5,000 Da is carried out, so as to obtain a third retentate and a third permeate;
- the second and the third retentate are mixed in order to obtain said mixture of oligosaccharides, said second retentate including oligosaccharides having molar weights resulting from the fractionation by ultrafiltration at a cutoff point between 15,000 and 50,000 Da, and said third retentate including the oligosaccharides having molar weights resulting from the fractionation by ultrafiltration at a cutoff point between 5,000 and 15,000 Da.

According to further particular features of the method:
- the extraction from flaxseed is preferably carried out in an aqueous solvent;
- the hydrolysis of the solution of mucilage is advantageously carried out at pH 2 and at a temperature of 80° C. for a period of 24 hours;
- preferably, said solution of mucilage is neutralized by adding, in an adequate amount, a strong base selected from the group comprising at least barium hydroxide and sodium hydroxide.

The present invention also relates to a mixture of neutral oligosaccharides extracted from flaxseed obtained by implementing the method according to the invention, said mixture including oligosaccharides having molar weights resulting from a fractionation by ultrafiltration at a cutoff point, on the one hand, between 15,000 and 50,000 Da and, on the other hand, between 5,000 and 15,000 Da.

In a particularly interesting way, said mixture comprises oligosaccharides the chain of which comprises at least fucose and/or arabinose and/or galactose and/or glucose and/or xylose.

Advantageously, said mixture includes a low rate of oligosaccharides the chain of which comprises rhamnose and a low rate of uronic acids.

The mixture of neutral oligosaccharides extracted from flaxseed can advantageously be used for dermatological or cosmetic purposes to fight against the effects of skin aging or to promote skin tissue repair.

Preferably, said mixture can also be used to stimulate:
- the proliferation of the fibroblasts;
- the chemotaxis of the fibroblasts;
- the cell migration of the fibroblasts;
- the synthesis of type III and/or type IV collagen by the fibroblasts.

The mixture of neutral oligosaccharides extracted from flaxseed also advantageously permits to stimulate the synthesis of lumican and to inhibit the synthesis of decorin by the fibroblasts.

Said mixture can also be used to induce the differentiation of the keratinocytes.

The mixture of neutral oligosaccharides extracted from flaxseed can namely also be used for promoting the healing of a wound.

The present invention also relates to a dermatological or cosmetic composition comprising a mixture of neutral oligosaccharides according to the invention and at least one cosmetically or dermatologically acceptable vehicle.

Advantageously, in the composition, the neutral oligosaccharide concentration is between 0.1 and 5 mg/mL.

According to a particular embodiment, the mixture of neutral oligosaccharides extracted from flaxseed according to the invention can also be used as a medicine, in particular for promoting the healing of the tissues, namely in chronic ulcers or after a surgery.

Other features and advantages of the invention will become clear from the following detailed description of the non-restrictive embodiments of the invention, with reference to the attached figures.

BRIEF DESCRIPTION OF THE SEVERAL VIEWS OF THE DRAWINGS

FIG. 1 is a table summarizing the characteristics of the samples E1 through E7 obtained from a flaxseed mucilage; the moieties E4 and E6, which are of particular interest, are surrounded in the table;

FIG. 9 corresponds to a photograph of agarose gels revealing the expression of the genes of the decorin and lumicanne proteoglycans in the fibroblasts in the presence or absence of oligosaccharides from flaxseed; the gene of GAPDH is used as a control.

DETAILED DESCRIPTION OF THE INVENTION

Figure 2:
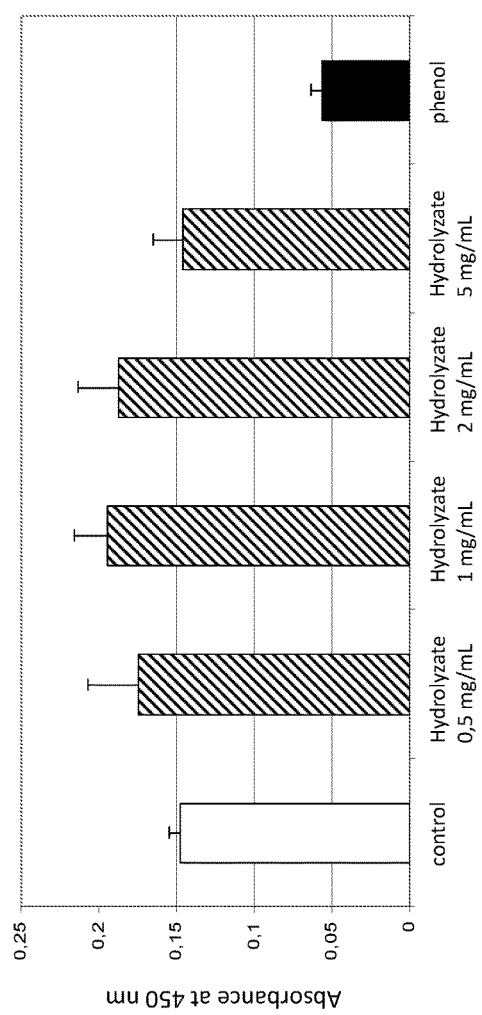
FIGS. 2A, B and C show, by means of histograms in which the number of live cells is assessed by colorimetry, the absence of cytotoxicity of the neutral oligosaccharides from flaxseed on the fibroblasts in the presence of different concentrations of oligosaccharides.
Figure 2:
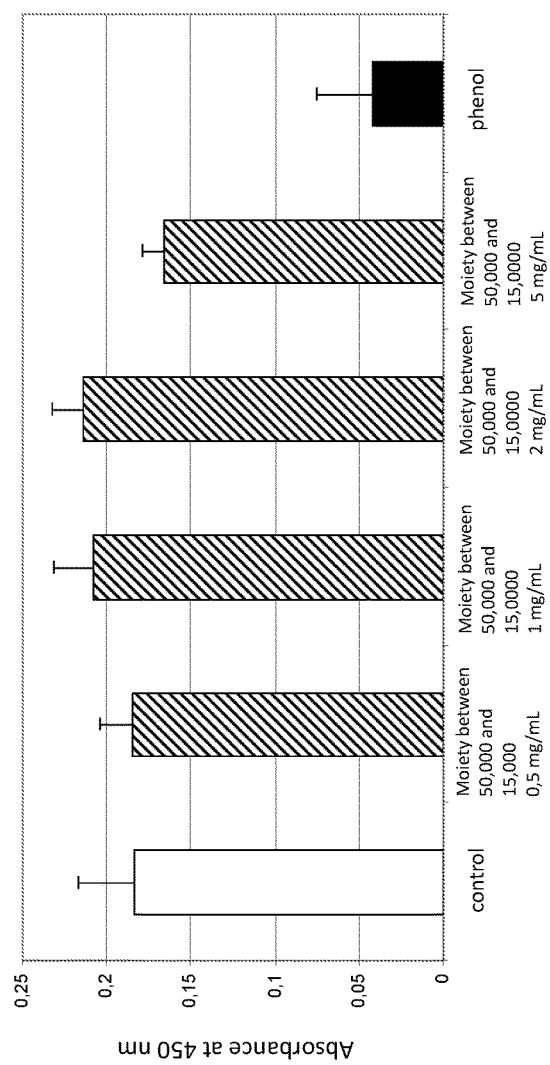
Figure 2:
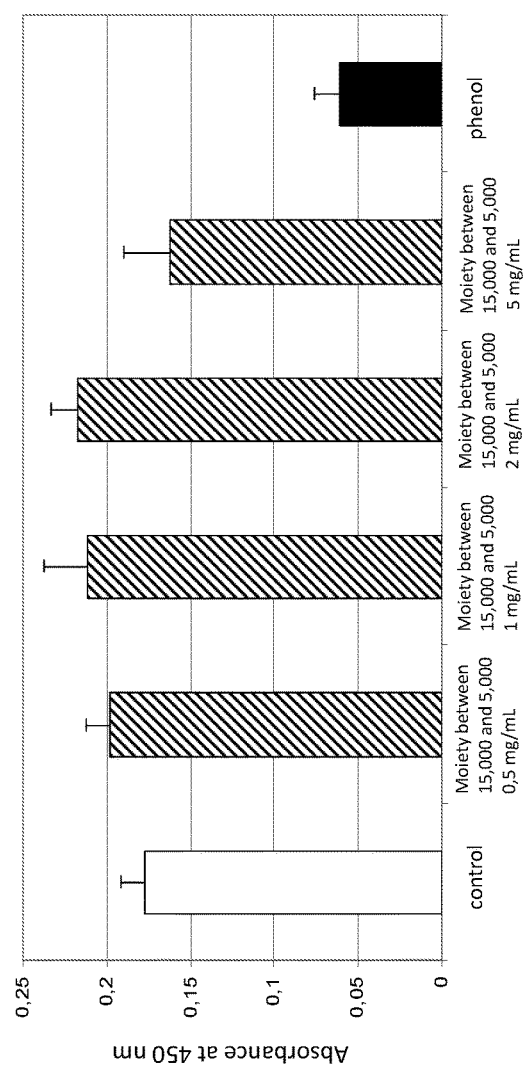

The present invention relates to a method for obtaining a mixture of neutral oligosaccharides from flaxseed, namely the *Linun usitatissimum* variety. Said mixture is advantageously obtained by controlled hydrolysis, then fractionation from a solution of mucilage from flaxseed, the latter being, in turn, obtained by extraction of said seeds in a solvent.

In the following description, by "oligosaccharide" is understood any osidic oligomer or polymer resulting from the hot acid hydrolysis of the mucilage and the molar weight of which permits passing through the ultrafiltration at 50,000 Da.

By "neutral oligosaccharide" is understood an oligosaccharide that includes no charge and no N-acetyl residues.

By "mucilage" is understood a plant substance comprised of osidic polymers, in particular polysaccharides surrounding namely the flaxseed.

By "solution of mucilage" is understood the solution obtained after soaking the flaxseed in a solvent, namely an aqueous solvent, for example water, and largely comprised of osidic polymers.

The method according to the invention advantageously permits to obtain a mixture of neutral oligosaccharides extracted from flaxseed including oligosaccharides having molecular weights resulting from a fractionation by ultrafiltration at a cut-off point, on the one hand, between 15,000 and 50,000 Da and, on the other hand, between 5,000 and 15,000 Da.

The invention also relates to a mixture of neutral oligosaccharides extracted from flaxseed obtained by implementing the method.

The present invention also relates to a composition, namely for cosmetic or dermatological use, and including a mixture of neutral oligosaccharides extracted from flaxseed obtained by the present method. Besides these oligosaccharides, said composition also advantageously includes at least one cosmetically or dermatologically acceptable vehicle.

The composition according to the invention may be either in the form of a cream, a gel, a lotion, a serum, a foam or an ointment.

Said composition is more particularly intended to be applied on the skin or also at the level of the superficial body growths.

The skin is a complex organ covering the entire body. It ensures several functions necessary for the survival of the body, namely the protection against any external aggression, whether it be physical, chemical or biological.

The skin is comprised of three main layers: the surface portion, the epidermis, followed by a thicker layer, the dermis, and the innermost layer, the hypodermis, in which the cells interact with each other in order to ensure the functions of the skin.

The epidermis is the layer directly into contact with the external environment. It protects the body by preventing the entry of pathogens and by maintaining the water and the nutrients inside. It has an average thickness of 100 μm, but it can vary considerably depending on the region of the body and the level of keratinization.

The main cell of the epidermis is the keratinocyte. It has many roles, namely in inflammatory and immune skin responses, thus forming a protective barrier.

The epidermis is separated from the dermis by a membrane, the so-called basal membrane, the main component of which is the type IV collagen.

The dermis is the layer that provides the skin with flexibility and resistance. Its thickness varies considerably depending on the anatomical location.

The dermis is mainly comprised of connective tissues that make it compressible and resilient. It constitutes a support for the various skin appendages, such as the blood vessels, the hair, the nerve endings and the sebaceous and sweat glands.

These appendages are surrounded by fibers mainly formed of type I and III collagen, which provide the dermis with softness and flexibility.

Collagen is one of the main components of the extracellular matrix. It is a protein that is namely synthesized during the process of tissue repair. However, the synthesis of collagen is increasingly less important depending on the age.

The fibroblasts are the majority cells of the dermis; they synthesize all types of fibers, namely the collagen fibers, as well as other components of the basal membrane.

The dermal fibroblasts are an essential component of the skin: they produce and organize the extracellular matrix of the dermis and communicate with other cell types, playing a crucial role in the regulation of the skin physiology.

The skin may suffer many internal and external aggressions over time. When the skin suffers damage or injury, a set of processes is implemented in order to repair this damage and restore a tissue as close as possible to the original tissue.

In particular, aging is a major factor of skin alterations. It changes the anatomical and histological structures and alters the cell functioning. The skin thus undergoes deep changes.

Skin aging results from a combination of different, complex and interrelated factors.

In particular, skin aging results from numerous cell alterations, such as a reduction of the telomeres, oxidative stress, a degradation of the DNA repair systems, plus external factors such as sun exposure, pollution, climate aggressions, but also the consumption of alcohol or tobacco, or also food.

Epidermal aging is primarily symptomized by the reduction of its thickness. This atrophy is the result, on the one hand, of the accumulation of senescent keratinocytes and, on the other hand, of the progressive loss of the characteristic invaginations of the epidermis.

Basal keratinocytes show a disparity in size and shape, suggesting morphological changes as well as a reduction of their proliferative capacity. Moreover, epidermis regeneration capacity, due to a trauma, decreases with age.

Furthermore, the epidermal adhesion properties decline due to a decrease in the expression of beta-1 integrin involved in the adhesion of basal keratinocytes to the underlying basal lamina. The collagen IV of the basal lamina, which permits the cohesion of the dermal-epidermal junction and the adhesion of keratinocytes, also decreases during aging.

Finally, aging causes a decrease in the number of melanocytes and Langerhans cells, affecting the ability of epidermal protection against attacks.

During skin aging, the dermis is also the locus of a deep disorganization with an extracellular matrix that appears to be dense and slightly vascularized. Its atrophy is mainly due to a reduction in the number and size of fibroblasts, but especially of their ability to synthesize.

In particular, the collagen fibrils get a grainy appearance and the fibers become more compact. They dissociate and tend to be directed parallel to the surface of the dermis. The alterations of the collagen fibers as well as the elastic material, the change in proteoglycan content and the development of fibroblasts in the quiescent state without direct contact with the collagen bundles represent the main characteristics of an aging dermis.

All these histological and biochemical alterations have crucial functional consequences for the properties of the skin, causing less well-adapted responses to the various external aggressions.

Tissue repair is an example of natural response when a tissue is damaged by an external aggression. This process occurs systematically and takes place in three phases: inflammation, proliferation and maturation.

The early events during a tissue repair are characterized by an inflammatory phase, a vascular and cellular response. Among the latter can be observed the arrival of many endothelial and vascular inflammatory cells. This occurs through the production of factors that have chemo-attractant properties.

During the proliferation phase, the formation of a grainy tissue is the key event. Inflammatory cells, the fibroblasts, the molecules of the extracellular matrix (fibronectin, collagen, glycosaminoglycans and proteoglycans) form the granulation tissue. The latter forms 3 to 5 days after the attack and occurs after the inflammatory phase.

When the epithelium has been injured, the epidermal cells near the wound multiply and migrate to cover the healthy tissue. When the process is complete, the epidermal cells return to their original shapes and play their roles. During this phase, a fibroplasia occurs: the fibroblasts play a very important role in this step. They are responsible for the production of collagen (and more particularly of type III collagen), elastin, fibronectin and glycosaminoglycan. Furthermore, the fibroblasts migrate and proliferate.

The third phase is the maturation and remodeling phase, in which the dermal and epidermal repair ends.

During this phase occur a fiber maturation and a cell apoptosis, which leads to forming a tissue close to the original tissue. Remodeling occurs namely at the level of the collagen. Proteins, so-called metalloproteinases (MMPs), permit to control the amount of collagen deposited in an uncontrolled manner in the early phases of the process, while the synthesis of the collagen continues in order to reconstitute regular and orderly fibers. The inhibitors of these MMPs regulate the activity of these enzymes. A balance is thus created between the formation of the new collagen and the destruction of the old collagen. The initially deposited collagen III decreases sharply, giving way to collagen I.

With age, during skin aging, the tissue repair becomes less effective: in particular, the fibroblasts proliferate and migrate less, the collagen synthesis decreases.

The applicants have developed a method permitting to obtain a mixture of neutral oligosaccharides extracted from flaxseed (namely *Linum usitatissimum*), said mixture obtained by the process according to the invention allows, by its particular composition of oligosaccharides, a substantial improvement in the efficiency of processes implemented during tissue repair while promoting slowing the appearance of visible signs of skin aging.

The experiments and researches that have been conducted show that the mixture of oligosaccharides having molar weights resulting from a fractionation by ultrafiltration at a cut-off point, on the one hand, between 5,000 and 15,000 Da and, on the other hand, between 15,000 and 50,000 Da, and obtained by the method according to the invention is particularly interesting for improving the skin repair.

Such a mixture that preferably comprises a plurality of oligosaccharides is advantageously obtained by implementing the method according to the invention, starting from a solution of mucilage from flaxseed and has remarkable properties, permitting namely a positive action on the cells involved in the mechanisms of tissue repair, such as the fibroblasts and the keratinocytes.

According to a preferred embodiment, the mixture of neutral oligosaccharides extracted from flaxseed by implementing the method according to the invention can be used to promote wound healing, both in humans as well as in animals.

Thus, such a mixture may advantageously be incorporated into a medical device such as a patch or a bandage, the latter being intended to be applied at the level of any wound, in order to permit a faster healing of the latter.

In a particularly interesting manner, the mixture of oligosaccharides obtained by the present method can also be used as a medicine, whether in the field of human medicine or veterinary medicine.

In particular, said mixture of oligosaccharides can advantageously promote tissue healing, namely in chronic ulcers or following a surgical procedure, in particular thanks to its beneficial effect on the fibroblasts of the connective tissues.

The properties of the mixture of neutral oligosaccharides extracted from flaxseed, obtained through the method according to the invention, will be developed and illustrated in the examples below, in connection with the various attached figures.

Example 1: Method for Preparing Oligosaccharide Moieties

In the method according to the invention, a solution of mucilage is obtained by extracting yellow flaxseeds in a solvent and preferably at elevated temperature, for example at a temperature of about 80° C. Said flaxseeds proceed namely from *Linum usitatissimum* and the ratio between said seeds and the solvent, advantageously water, is preferably in the range of 1/10.

This extraction step is advantageously followed by a centrifugal separation, and a liquid extract is recovered and precipitated in an ethanolic medium, by implementing a ratio in the range of 1/4 between said extract and ethanol.

Advantageously, the extract is then again placed into a 2% solution for the hydrolysis step. This solution is hydrolysed at pH 2, preferably by adding sulfuric acid $H_2SO_4$. The hydrolysis reaction is preferably performed at a temperature in the range of 80° C., for a period of 24 hours.

However, the pH and temperature parameters as well as the duration of the hydrolysis can be adjustable, if required.

After the hydrolysis step, the solution is neutralized, for example by adding an adequate amount of a strong base selected from the group comprising namely barium hydroxide $Ba(OH)_2$ and sodium hydroxide NaOH.

It is however also possible to use any other base permitting to neutralize the solution of mucilage.

The solution is then submitted to a series of several ultrafiltration operations in order to be purified.

The first ultrafiltration of the solution is performed through a preferably mineral membrane having a porosity threshold of 50,000 Da (Carbosep, 6 mm diameter, trilobal, 6.8 $m^2$ surface). After this first ultrafiltration, preferably performed with a volume concentration factor varying between 5 and 7, a first retentate is obtained, which includes the compounds and molecules having molecular weights that do not pass the cut-off point of 50,000 Da, and a first permeate in which can be found the compounds having molecular weights exceeding this porosity threshold.

This first permeate is then submitted to a second ultrafiltration step, (preferably on a mineral membrane of 15,000 Da, InsideCéram, 20 mm diameter/13 channels, 0.8 m² surface) advantageously performed with a volume concentration factor between 4 and 8, and a second retentate and a second permeate are obtained.

The second permeate, obtained after the second step of ultrafiltration on a membrane of 15,000 Da, is submitted to another ultrafiltration step (preferably on a mineral membrane of 5,000 Da, InsideCéram, 20 mm/13 channels, 0.8 m² surface) for example performed with a volume concentration factor between 4 and 8. A third retentate and a third permeate are then obtained.

At the end of the ultrafiltration operations, 7 samples or moieties are thus obtained: the initial hydrolyzate (E1), the first retentate of 50,000 Da (E2), the first permeate of 50,000 Da (E3), the second retentate of 15,000 Da (E4), the second permeate of 15,000 Da (E5), the third retentate of 5,000 Da (E6) and the third permeate of 5,000 Da (E7).

More particularly, the samples of interest are samples designated with E4 (second retentate) and E6 (third retentate), comprising respectively oligosaccharides having high molar weights resulting from fractionation by ultrafiltration at a cutoff point, on the one hand, between 15,000 and 50,000 Da for E4 and, on the other hand, between 5,000 and 15,000 Da for E6.

These samples are left in liquid or lyophilized form.

Mixing the second and third retentates permits to obtain the mixture of oligosaccharides of interest.

Example 2: Characterization of Oligosaccharide Moieties

The samples have been analyzed by size exclusion chromatography (SEC) coupled to light scattering (MALS: Multi Angle Light Scattering) and a differential refractometric detector (DRI: Differential Refractive Index). The analysis line is comprised of a degasser (Shimadzu DGU-20A3, Japan), an HPLC pump (Shimadzu LC10Ai, Japan) at a flow rate of 0.5 mL/min, an automatic injector (Shimadzu SIL-20A, Japan), two Shodex columns mounted in series (OHpack SB802.5 and SB804), a multi-angle light scattering detector: MALS (Dawn EOS, Wyatt Technology Corp., USA), provided with a K5 cell 50 µL and 18 measuring diodes and a differential refractometric detector (RID 10A Shimadzu, Japan). The moieties have been characterized using the Astra 6 software (Wyatt Technology), using the order 1 Zimm method. The refractive index increment (dn/dc) used is 0.15 ml/g, traditional mean value for an oligosaccharide or a polysaccharide.

The solutions with concentrations of 2, 5, 10 or 20 g/L of oligosaccharides, depending on the moieties, are prepared either by solubilization in a 0.15 mol/L NaCl solution of the lyophilized mixture of oligosaccharides, or by dilution of the mixture in liquid form, taking into consideration the dry extract of the initial solution. A 30 ml volume of these solutions is taken and filtered under vacuum for 10 minutes using a regenerated cellulose membrane with a 0.45 µm porosity of the Millipore brand in order to remove any over-scattering insoluble compound and to obtain a beautiful basic line.

The integration of the refractometric and light-scattering peaks yields, for the second retentate (E4) resulting from fractionation by ultrafiltration at a cut-off point between 15,000 and 50,000 Da, a number average molecular weight of 17,000 g/mol and an average molecular weight of 31,000 g/mol (measuring uncertainties+/−2,000 g/mol).

For the third retentate (E6), resulting from the cutoff points 5,000 and 15,000 g/mol, the number and weight average molecular weights are 4,000 and 5,000 g/mol, respectively, with a measuring uncertainty of +/−1,000 g/mol.

The measuring uncertainties are due to the low light-scattering signal because of the low molecular weights.

The other results obtained are listed in the table of FIG. 1.

In this table, MS corresponds to the recovered dry mass. The term "ash/MS" corresponds to the ash content compared to the dry material of the sample.

The dry material content is determined by drying in an oven under the following conditions: at least 16 hours at 103° C.

The ash content is determined by treating the sample in a muffle furnace under the following conditions: temperature gradient (103° C., 550° C., 700° C.) for 20 hours.

The term "Prot" relates to the percentage of protein determined by the Kjeldahl method.

The "uronic" column permits to illustrate the amount of uronic acids being recovered, determined by colorimetry.

The percentage of oligosaccharides of each sample can be determined by subtracting the percentage of free sugars from the percentage of total sugars.

It is remarkable that the percentage of uric acid in the samples being analyzed is low, preferably less than 12%, and even more preferably less than 5%, this namely in the moieties of interest E4 and E6.

Furthermore, after analysis of the oligosaccharide profiles in the different samples (results not shown), it turns out that, in the second and third retentate containing the mixture of oligosaccharides of interest, the oligosaccharide chains contain only a small amount of rhamnose.

Indeed, the ionized osidic chains including rhamnose and uronic acids are little affected by the hydrolysis, that is why the mixture of oligosaccharides contains few of these molecules.

Thus, advantageously, the neutral moiety of the oligosaccharides, which constitutes the most active moiety, is the most affected by the hydrolysis step of the method according to the invention.

The oligosaccharide profile has also been analyzed in the samples. It has namely been found that the percentage of oligosaccharides in each of the samples is between 40 and 80% by mass compared to the total weight of said sample.

Furthermore, it has been demonstrated that the chains of the oligosaccharides present in the samples namely comprised the following particular oses: fucose, arabinose, galactose, glucose and xylose.

Effects of the oligosaccharide moieties on the skin cells.

The different samples E1 through E7 have been tested in order to assess their effects, in particular on the cells involved namely in the skin repair process.

Example 3: Absence of Cytotoxicity of the Moieties Obtained on the Fibroblasts and the Keratinocytes Dermal fibroblasts and epidermal keratinocytes from adult skins (skin fragments obtained during surgery or commercial cell cultivations (Lonza (registered TM), Switzerland)) have been cultivated in vitro. The experiments have been conducted on cells in primary cultivations so as to approximate as well as possible the conditions existing in vivo.

The studies conducted on these cell cultivations have permitted to show that, up to a concentration of about 5 mg/ml of oligosaccharides, the samples including oligosaccharides extracted from flaxseed are not cytotoxic for the cells of the type dermal fibroblasts and epidermal keratinocytes.

The results obtained are visible on the histograms of the attached FIG. 2. This shows the number of living cells, represented by the absorbance at 450 nm on the ordinates, when these cells are in the presence of the various oligosaccharide moieties.

More particularly, the moieties that have been tested are the hydrolyzate E1 (FIG. 2A), the second retentate E4 (FIG. 2B—moiety comprising the oligosaccharides the molecular weights of which are between the ultrafiltration cutoff points of 15,000 and 50,000 Da) and the retentate E6 (FIG. 2C—moiety comprising the oligosaccharides the molecular weights of which are between the ultrafiltration cutoff points of 5,000 and 15,000 Da).

These moieties have been tested at different concentrations (0.5; 1.0; 2.0 and 5.0 mg/mL) on adult human dermal fibroblasts cultivated in vitro and arrived at confluence. The control corresponds to the cytotoxicity of the cultivation medium alone and the cytotoxic control corresponds to cells cultivated in phenol (0.1%).

The WST-1 test is used for evaluating the cytotoxicity of the various samples on the cells.

The results show that the samples that have been tested are not cytotoxic for the cells, and do not cause damage, on the one hand, on the fibroblasts and, on the other hand, on the keratinocytes (data not shown) up to an oligosaccharide concentration of 5 mg/mL.

In addition, other experiments being conducted have shown that there were no adverse effects due to the exposure of fibroblasts and keratinocytes to oligosaccharide moieties having a concentration of 1 mg/mL during a period of 48 hours (results not shown).

Example 4: Effect of Oligosaccharide Moieties on the Proliferation of the Fibroblasts It has been shown that, in addition to having no cytotoxic effects on the cells, the oligosaccharides extracted from flaxseed and obtained by the method of the invention permit an efficient stimulation of the proliferation of the dermal fibroblasts.

Figure 3:
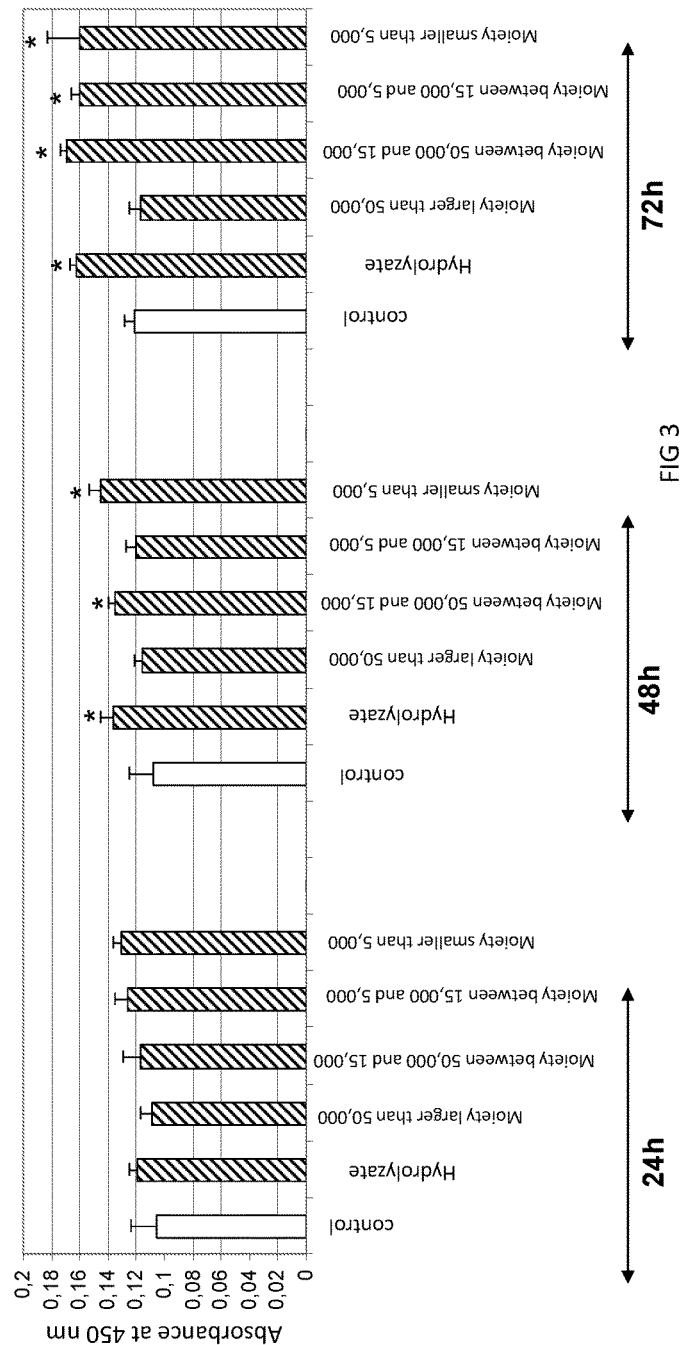
FIG. 3 shows the effect of neutral oligosaccharides from flaxseed on the proliferation of fibroblasts after different incubation times (24, 48 and 72 hours)

The positive effect of the neutral oligosaccharides from flaxseed on the fibroblasts is illustrated in FIG. 3. The cells have been exposed to oligosaccharide moieties having a concentration of 1 mg/mL, and the proliferation of the fibroblasts is measured by implementing the WST-1 test at different exposure times (24, 48 and 72 hours).

The results show that the oligosaccharide moieties that have been tested induce an increase in proliferation of the dermal fibroblasts. The stimulation of the proliferation is greater after 48 or 72 hours of incubation of the cells in the presence of the oligosaccharides extracted from flaxseed.

Studies on the proliferation of the fibroblasts depending on the concentration of the oligosaccharide moieties have also been conducted. The results (not shown) permit to observe that the stimulation of the proliferation is observed as from 0.5 mg/mL for the samples E4 and E6.

Example 5: Effect of the Neutral Oligosaccharides from Flaxseed on Chemotaxis It has also been demonstrated that the neutral oligosaccharides extracted from flaxseed obtained by the method according to the invention have a significant chemotactic activity on the fibroblasts. This effect is particularly advantageous for tissue repair.

Therefore, adult human dermal fibroblasts have been cultivated in vitro in Transwell (registered TM) inserts comprising a membrane, said fibroblasts being incubated for 24 hours in the presence or absence (control) of various samples comprising oligosaccharides extracted from flaxseed at a concentration of 1 mg/mL.

The chemotaxis of the dermal fibroblasts is assessed by counting the number of cells that pass through the membrane of the insert.

Figure 4:
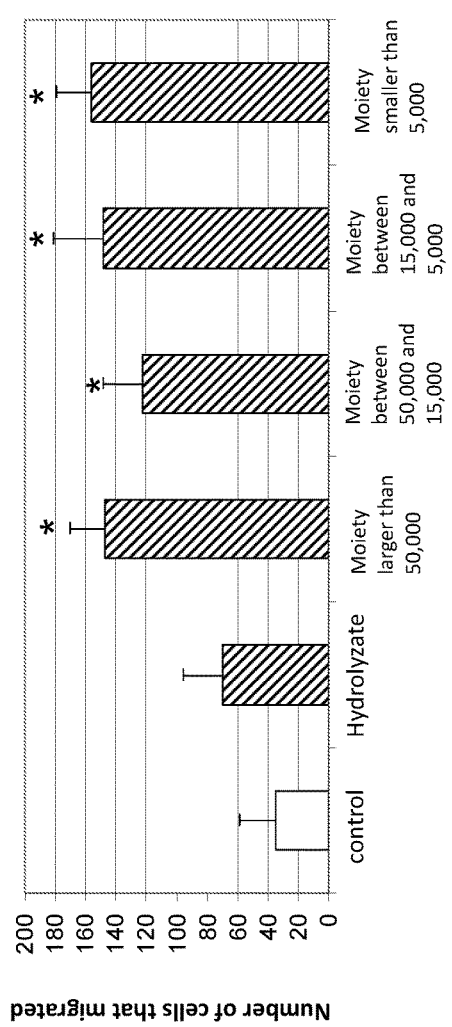
FIG. 4 shows, by means of histograms, the number of cells having migrated depending on their exposure or not to neutral oligosaccharides extracted from flaxseed.
Figure 5:
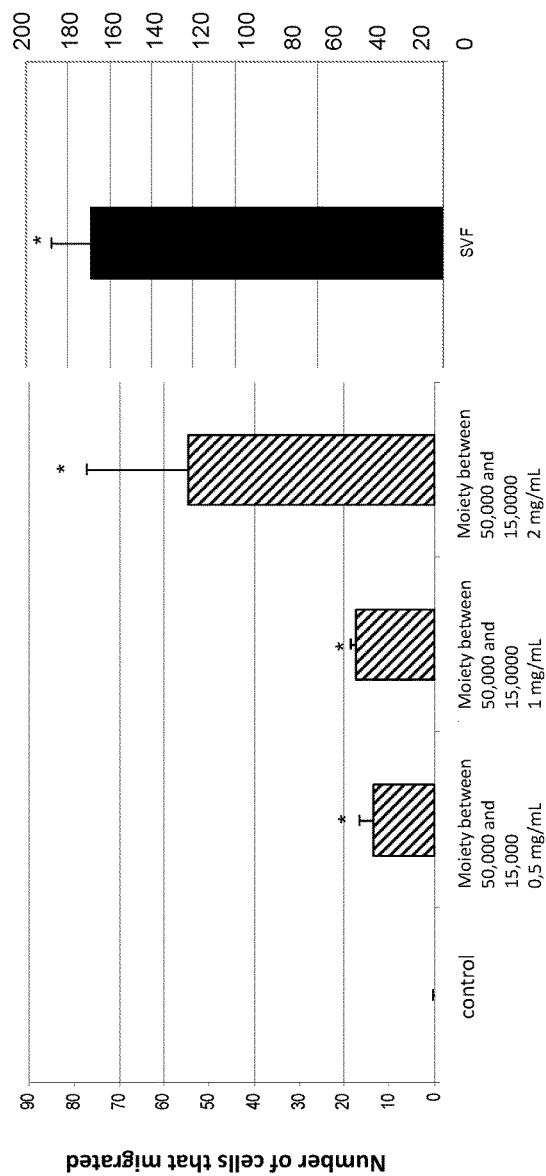
FIG. 5 also shows the migration of the fibroblasts depending on different concentrations of neutral oligosaccharides extracted from flaxseed.

The results, visible in FIG. 4, clearly show that the neutral oligosaccharides from flax obtained by the method according to the invention induce an increase in the chemotaxis of the dermal fibroblasts. Other experiments that have been conducted have permitted to show that the chemotactic effect is visible at a very low concentration of oligosaccharides (0.5 mg/mL), this chemotactic effect increasing with higher concentrations of oligosaccharides. The results are illustrated in FIG. 5.

Example 6: Effect of Oligosaccharides from Flaxseed on the Cell Migration

The cell migration of the dermal fibroblasts over time has been measured in the presence and absence of neutral oligosaccharides from flaxseed and obtained by the method according to the invention. These compounds have been tested on fibroblasts and the migration of the latter has been monitored over time.

Figure 6:
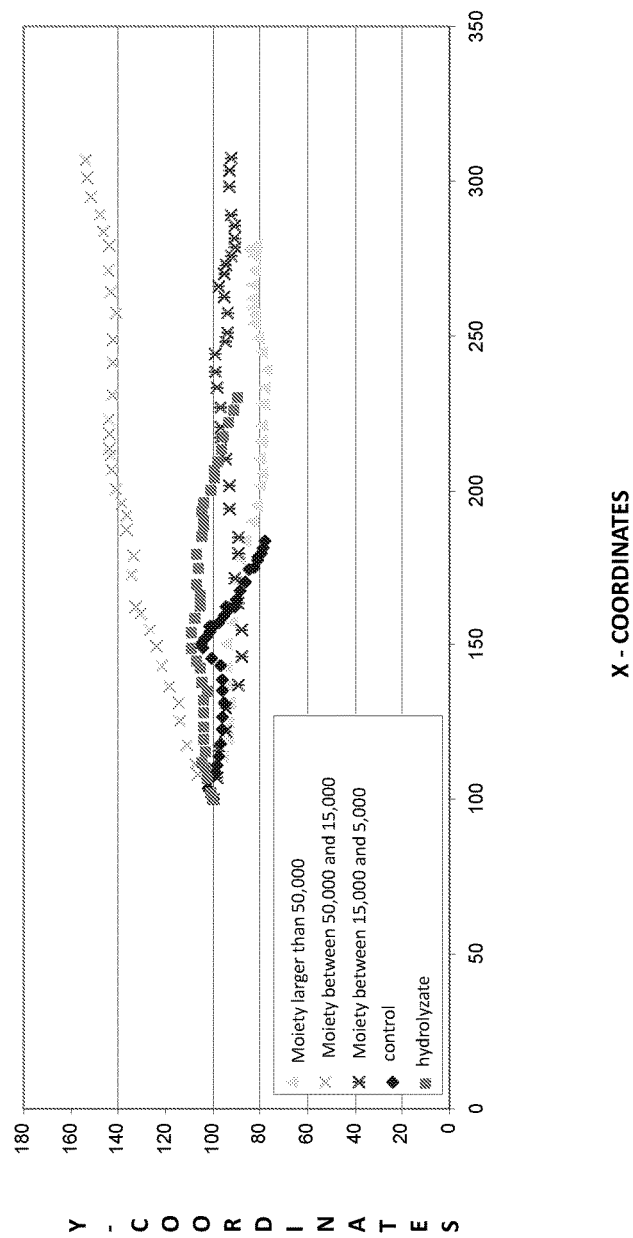
FIG. 6 is a graphical representation of the path of the fibroblasts in the presence or absence of oligosaccharide moieties.

The results are illustrated in FIG. 6. Adult human dermal fibroblasts have been cultivated in vitro in Ibidi (registered trademark) inserts permitting to implement the conditions of an artificial wound.

The fibroblasts have been incubated in the presence of a concentration of oligosaccharides of 1 mg/ml and the cell migration has been monitored for 48 hours by means of a video-microscope. The trajectory of the cells is thus reconstituted.

It is clearly visible that the oligosaccharide moieties obtained by implementing the method according to the invention and having neutral oligosaccharides having molecular weights resulting from the fractionation by ultrafiltration at a cutoff point between 5,000 and 15,000 Da and between 15,000 and 50,000 Da permit a significant cell migration, which induces a much faster closing of an artificial injury in vitro.

Example 7: Effect of the Oligosaccharides from Flaxseed on the Synthesis of Type III and Type IV Collagen It has been shown here that the moieties having neutral oligosaccharides extracted from flaxseed induce a significant increase of collagen synthesis, especially of type III collagen, which is synthesized primarily during the tissue repair by the fibroblasts.

Adult human dermal fibroblasts have been cultivated in vitro and have been activated for 24 hours (FIG. 7A) and 48 hours (FIG. 7B) in the presence and absence of oligosaccharide moieties extracted from flaxseed, the latter having a concentration of 1 mg/mL. The supernatants of the cultivation have been recovered, and the amount of type III collagen has been determined by a determination using an ELISA commercial kit.

Figure 7:
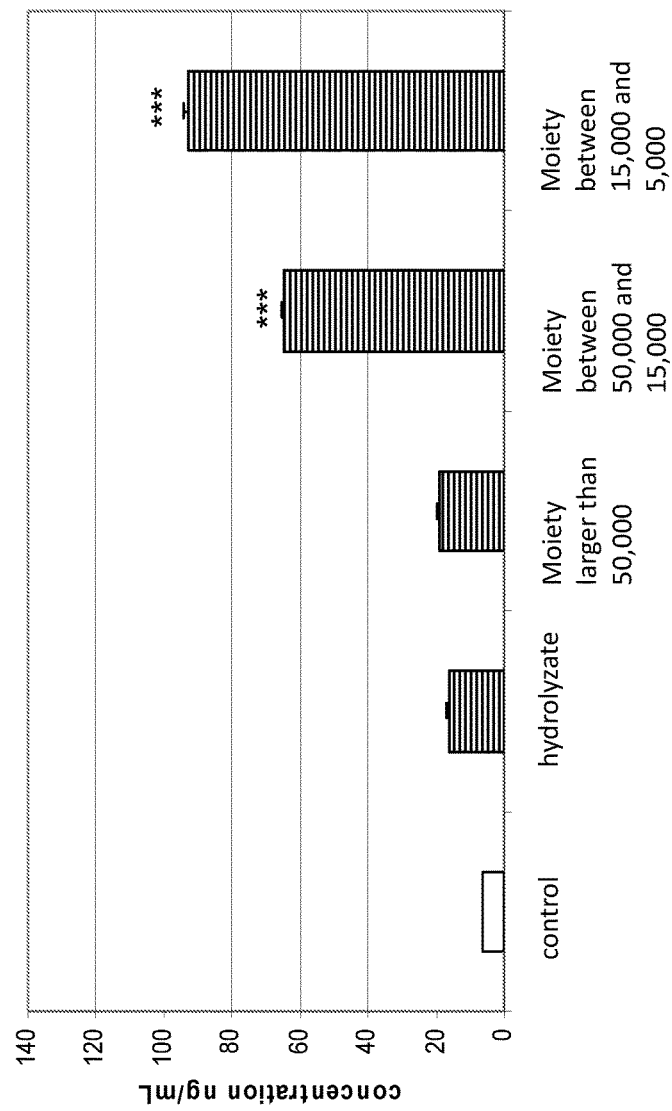
FIGS. 7A and 7B graphically represent, in the form of histograms, the synthesis of type III collagen in the presence of oligosaccharides for a period of 24 (FIG. 7A) or 48 (FIG. 7B) hours.
Figure 7:
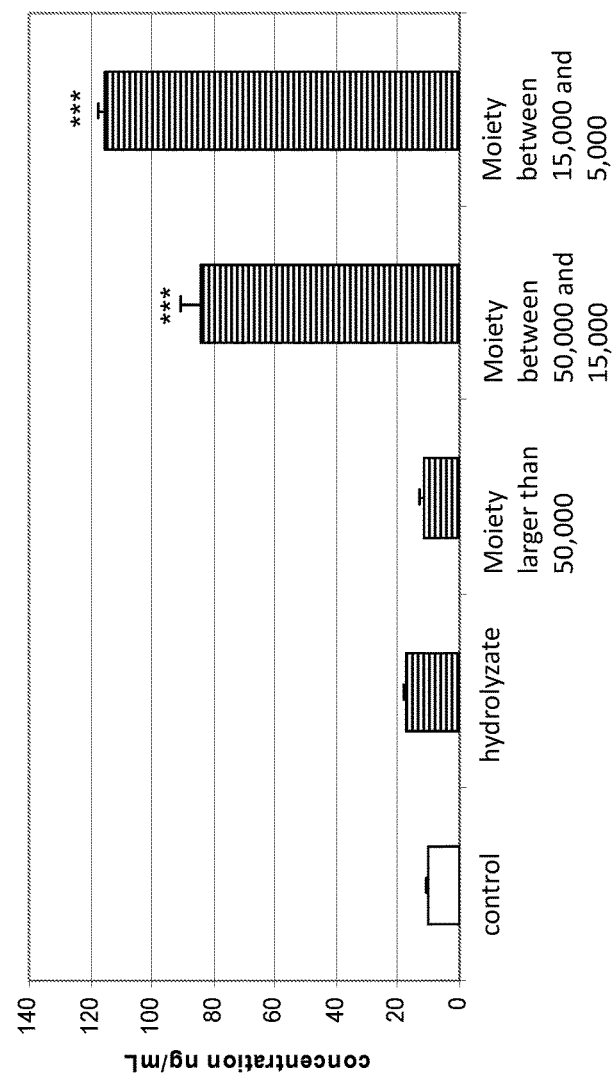

The results of the synthesis of type III collagen are visible in FIG. 7.

This figure illustrates very well that the samples including, on the one hand, neutral oligosaccharides having molecular weights resulting from the fractionation by ultrafiltration at a cutoff point between 5,000 and 15,000 Da and, on the other hand, between 15,000 and 50,000 Da, said samples being obtained by the method according to the invention, permit a significant increase of the synthesis of type III collagen by the fibroblasts.

Other experiments that have been conducted have also permit to show that the neutral oligosaccharides extracted from flaxseed permit an increase of the synthesis of type IV collagen by the fibroblasts.

More specifically, human dermal fibroblasts have been cultivated in vitro to the confluence, then the cells have been incubated for 24 hours with various samples, namely with the oligosaccharide moieties corresponding to the second and third permeates and obtained by implementing the method according to the invention. The concentration of the moieties is 1 mg/mL.

The supernatants of the cultivation are then recovered, and the collagen IV is analyzed in the supernatant and in the cell layer.

Figure 8:
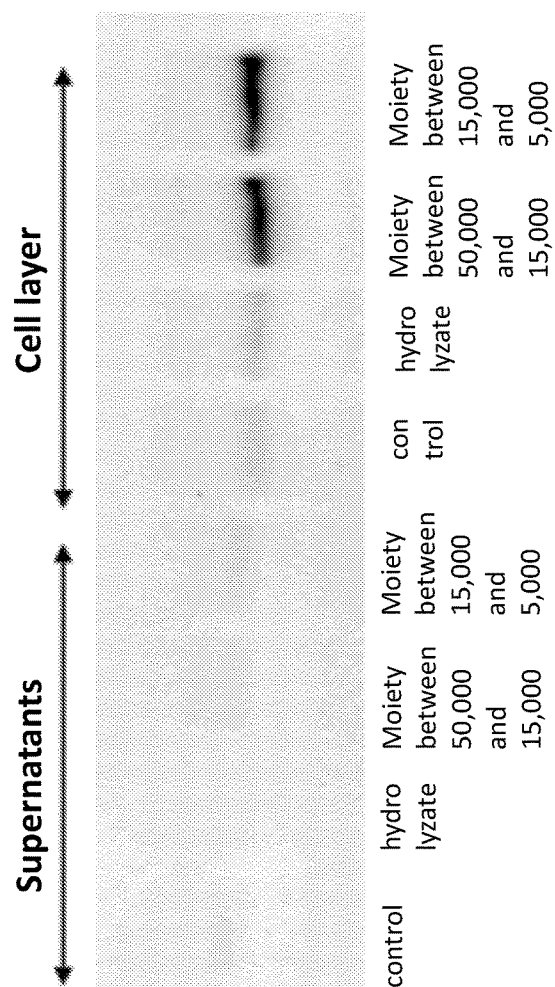
FIG. 8 corresponds to a photograph of western blot membranes revealing the expression of the type IV collagen in the fibroblasts in the presence or absence of oligosaccharides from flaxseed.

The results, shown in FIG. 8, show that the oligosaccharide moieties resulting from a fractionation by ultrafiltration at a cut-off point, on the one hand, between 15,000 and 50,000 Da and, on the other hand, between 5,000 and 15,000 Da are capable of activating the synthesis of collagen IV. Such an effect is particularly advantageous, since collagen IV constitutes one of the essential components of the basal membranes and that the synthesis of this component tends to decrease during aging.

Example 8: Effects of the Neutral Oligosaccharides Extracted from Flaxseed on the Synthesis of the Small Proteoglycans The compounds called proteoglycans, and namely the SLRPs (Small Leucine-rich Proteoglycans), play an important role in the regulation of the cell activity and in the organization of the functional properties of the skin.

In particular, decorin and lumican are important proteoglycans. Decorin is abundant in adult skin and plays a key role in the regulation of the homeostasis. The amount of decorin in the skin increases with age. Instead, the amount of lumican tends to decrease with age. Lumican plays a role in the preservation of the functional properties of the skin.

Experiments have been conducted to determine the impact of the neutral oligosaccharides extracted from flaxseed, and obtained by the present method, on the synthesis of these small proteoglycans.

The fibroblasts have been cultivated for 24 hours in the presence of neutral oligosaccharides extracted from flax at a concentration of 1 mg/mL.

The RNAs have then been extracted from the fibroblasts and a series of RT-PCRs have been conducted to evaluate the expression of the genes encoding the synthesis of decorin and lumican. The expression of the gene of the GAPDH is used as a positive control.

The results are shown in the attached FIG. 9. They show that the neutral oligosaccharides extracted from flax permit to induce a decrease in the synthesis of decorin by the dermal fibroblasts, while, on the contrary, the expression of lumican increases.

Hence, the bringing into contact of an aged skin with neutral oligosaccharides obtained by the present method and having namely molar weights resulting from the fractionation by ultrafiltration at a cutoff point between 5,000 and 15,000 Da or between 15,000 and 50,000 Da permits to approach the phenotype of a younger skin.

Example 9: Effects of the Neutral Oligosaccharides Extracted from Flaxseed on the Keratinocytes It has been observed, by optical microscopy, that the moieties including neutral oligosaccharides extracted from flaxseed have a positive effect on the epidermal keratinocytes.

In particular, the neutral oligosaccharides induce a differentiation of the keratinocytes, the latter being more particularly characterized by a change in morphology.

The observations through a microscope have been confirmed by immunocytochemical experiments, in which various differentiation markers have been used, such as involucrin, marker of the grainy layer, or also filaggrin and loricrin, markers of the stratum corneum of the epidermis (results not shown). The appearance of these markers in the keratinocytes is strongly stimulated by the neutral oligosaccharides obtained by the method according to the invention.

The stimulation of the differentiation of the keratinocytes is beneficial for the skin as it increases its protection against external aggressions.

Of course, the invention is not restricted to the examples illustrated and described above that can have variants and modifications without departing from the scope of the invention.

What is claimed:

1. A method for obtaining a composition of neutral oligosaccharides extracted from flaxseed, said method including the following steps:
   carrying out a hydrolysis at acidic pH on a solution of flax mucilage, said flax mucilage being obtained by extraction from flaxseed in a solvent;
   neutralizing said solution by adding a base in an adequate quantity so as to form a neutralized solution;
   carrying out a first ultrafiltration of said neutralized solution through a membrane with a porosity of 50,000 Da so as to obtain a first retentate and a first permeate;
   carrying out a second ultrafiltration of said first permeate through a membrane with a porosity of 15,000 Da so as to obtain a second retentate and a second permeate;
   carrying out a third ultrafiltration of said second permeate through a membrane with a porosity of 5,000 Da so as to obtain a third retentate and a third permeate; and
   mixing said second retentate and said third retentate in order to obtain a mixture of oligosaccharides between 5,000 and 15,000 Da, said second retentate being comprised of oligosaccharides having molar weights resulting from fractionation by said second ultrafiltration at a cutoff point between 15,000 and 50,000 Da, and said third retentate being comprised of oligosaccharides having molar weights resulting from fractionation by said third ultrafiltration at a cutoff point between 5,000 and 15,000 Da.

2. The method for obtaining said composition of neutral oligosaccharides, according to claim 1, wherein said extraction from flaxseed is carried out in an aqueous solvent.

3. The method for obtaining said composition of neutral oligosaccharides, according to claim 1, wherein the step of carrying out said hydrolysis is at pH 2 and at a temperature of 80° C. for a period of 24 hours.

4. The method for obtaining said composition of neutral oligosaccharides, according to claim 1, wherein said base in the step of neutralizing is selected from a group consisting of barium hydroxide and sodium hydroxide.

5. A composition comprising:
mixture of oligosaccharides, according to claim 1, said oligosaccharides having molecular weights resulting from a fractionation by said first ultrafiltration at a cutoff point between 15,000 and 50,000 Da and molecular weights resulting from a fractionation by said second ultrafiltration between 5,000 and 15,000 Da.

6. The composition, according to claim 5, wherein said oligosaccharides have a chain comprised of at least one of a group consisting of: fucose, arabinose, galactose, glucose, and xylose.

7. The composition, according to claim 5, wherein said oligosaccharides are comprised of a low rate of oligosaccharides having a chain comprised of rhamnose and a rate of uronic acids less than 12%.

8. The method for obtaining said composition of neutral oligosaccharides, according to claim 1, further comprising the steps of:
applying said mixture of oligosaccharides between 5,000 and 15,000 Da to skin so as to fight effects of skin aging and promote skin tissue repair.

9. The method for obtaining said composition of neutral oligosaccharides, according to claim 1, further comprising the step of:
applying said mixture of oligosaccharides between 5,000 and 15,000 Da to dermis so as to stimulate proliferation of fibroblasts.

10. The method for obtaining said composition of neutral oligosaccharides, according to claim 1, further comprising the step of:
applying said mixture of oligosaccharides between 5,000 and 15,000 Da to dermis so as to stimulate chemotaxis of fibroblasts.

11. The method for obtaining said composition of neutral oligosaccharides, according to claim 1, further comprising the step of:
applying said mixture of oligosaccharides between 5,000 and 15,000 Da to dermis so as to stimulate cell migration of fibroblasts.

12. The method for obtaining said composition of neutral oligosaccharides, according to claim 1, further comprising the step of:
applying said mixture of oligosaccharides between 5,000 and 15,000 Da to skin so as to stimulate synthesis of a collagen by fibroblasts, said collagen selected from a group consisting of: type III collagen and type IV collagen.

13. The method for obtaining said composition of neutral oligosaccharides, according to claim 1, further comprising the step of:
applying said mixture of oligosaccharides between 5,000 and 15,000 Da to skin so as to stimulate synthesis of lumican and so as to inhibit synthesis of decorin by fibroblasts.

14. The method for obtaining said composition of neutral oligosaccharides, according to claim 1, further comprising the step of:
applying said mixture of oligosaccharides between 5,000 and 15,000 Da to skin so as to induce differentiation of keratinocytes.

15. The method for obtaining said composition of neutral oligosaccharides, according to claim 1, further comprising the step of:
applying said mixture of oligosaccharides between 5,000 and 15,000 Da to skin so as to promote healing of a wound.

16. The composition, according to claim 5, further comprising: at least one cosmetically or dermatologically acceptable vehicle.

17. The composition according to claim 16, wherein concentration of said mixture of oligosaccharides between 5,000 and 15,000 Da is between 0.1 and 5 mg/mL.

18. The method for obtaining said composition of neutral oligosaccharides, according to claim 1, further comprising the step of:
applying said mixture of oligosaccharides between 5,000 and 15,000 Da to skin as a medicine.

19. The method for obtaining said composition of neutral oligosaccharides, according to claim 18, the method further comprising the step of:
applying said mixture of oligosaccharides between 5,000 and 15,000 Da to skin so as to promote healing of tissues.

* * * * *